United States Patent [19]

Allen

[11] Patent Number: 5,204,063
[45] Date of Patent: Apr. 20, 1993

[54] ELUENT RELEASE SYSTEM AND AUTOMATED ASSAY DEVICE

[75] Inventor: Michael P. Allen, Sunnyvale, Calif.

[73] Assignee: Chemtrak, Inc., Sunnyvale, Calif.

[21] Appl. No.: 806,579

[22] Filed: Dec. 12, 1991

[51] Int. Cl.$^5$ .................. G01N 21/79; G01N 31/22
[52] U.S. Cl. ........................... 422/58; 422/56; 422/57; 422/61; 422/104; 436/169; 436/170; 436/164; 435/810
[58] Field of Search .............. 422/58, 56, 55, 57, 422/61, 99, 104; 436/169, 170, 164; 435/810

[56] References Cited

U.S. PATENT DOCUMENTS

| | | | |
|---|---|---|---|
| 4,959,324 | 9/1990 | Ramel et al. | 436/169 |
| 4,981,786 | 1/1991 | Dafforn et al. | 435/7 |
| 4,999,287 | 3/1991 | Allen et al. | 435/11 |
| 5,009,846 | 4/1991 | Gavet et al. | 422/56 |
| 5,114,678 | 5/1992 | Crawford et al. | 422/99 |

Primary Examiner—James C. Housel
Assistant Examiner—Long V. Le
Attorney, Agent, or Firm—Bertram I. Rowland

[57] ABSTRACT

Improved self-contained automated assay devices are provided which allow for reliable release of eluent solution upon opening of a pouch with scoring teeth, so that the solution is transferred to a well for carrying out the assay. The improvements comprise using a bibulous member which is moved into the pouch to initiate eluent solution transport or providing for a sudden shock to the solution to initiate flow.

7 Claims, 4 Drawing Sheets

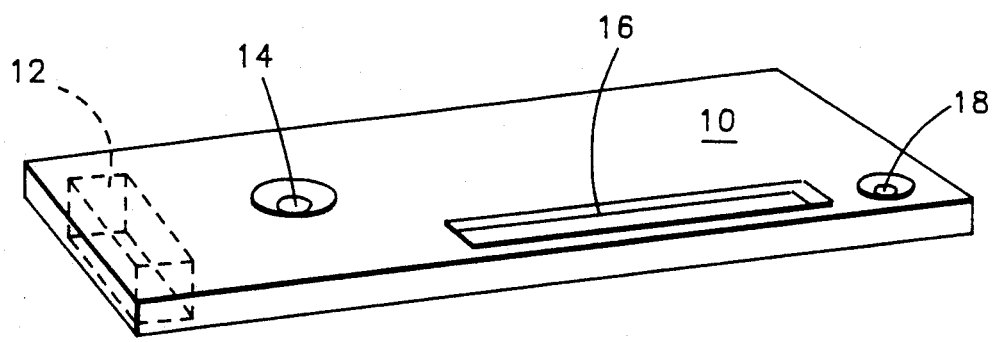
FIG.—1A
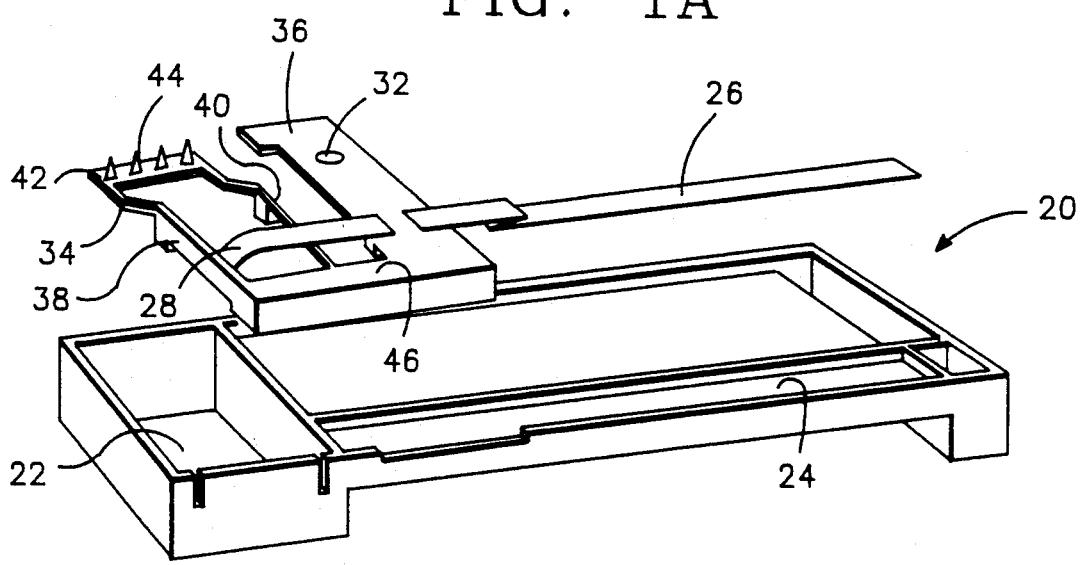
FIG.—1B
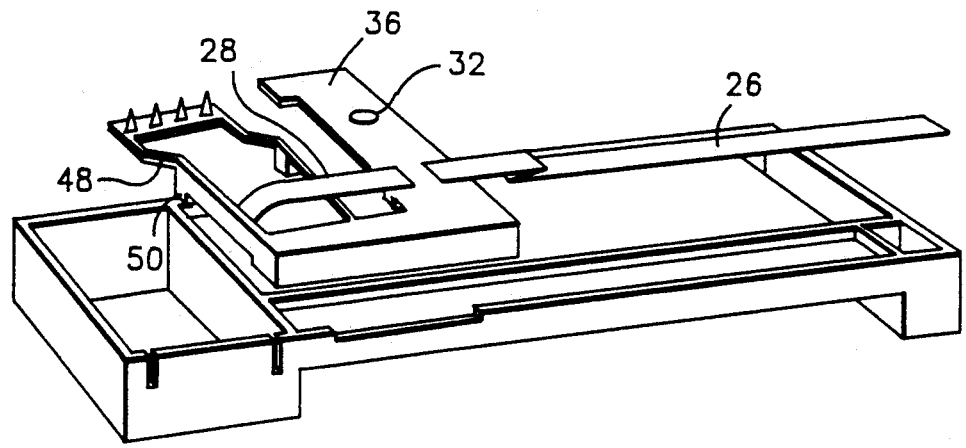
FIG.—1C

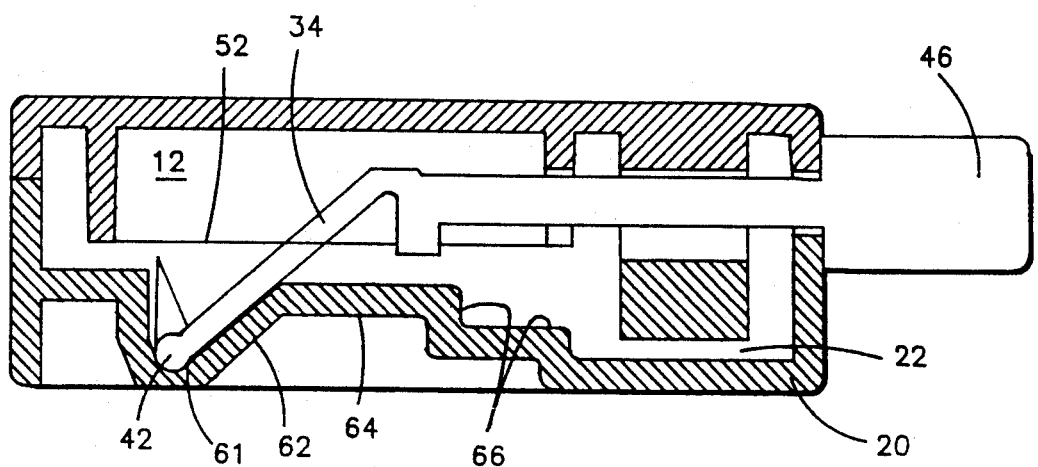
FIG.—4
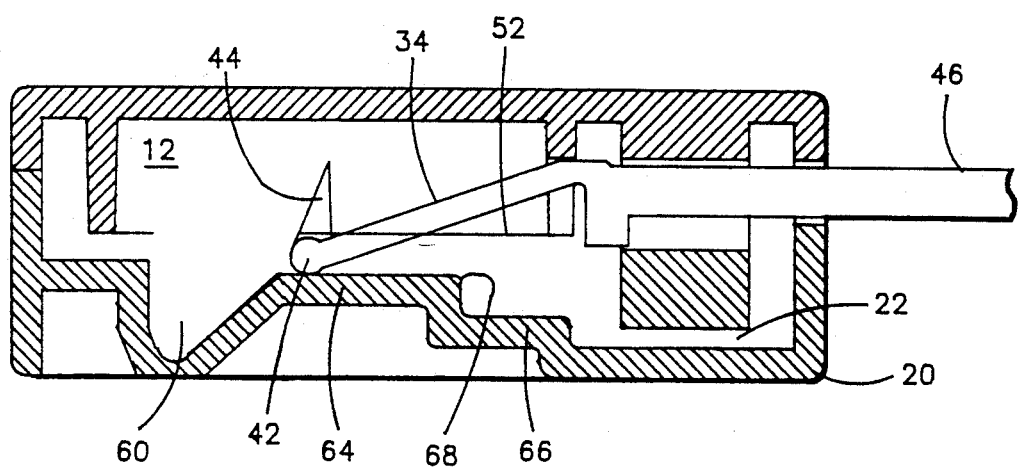
FIG.—5

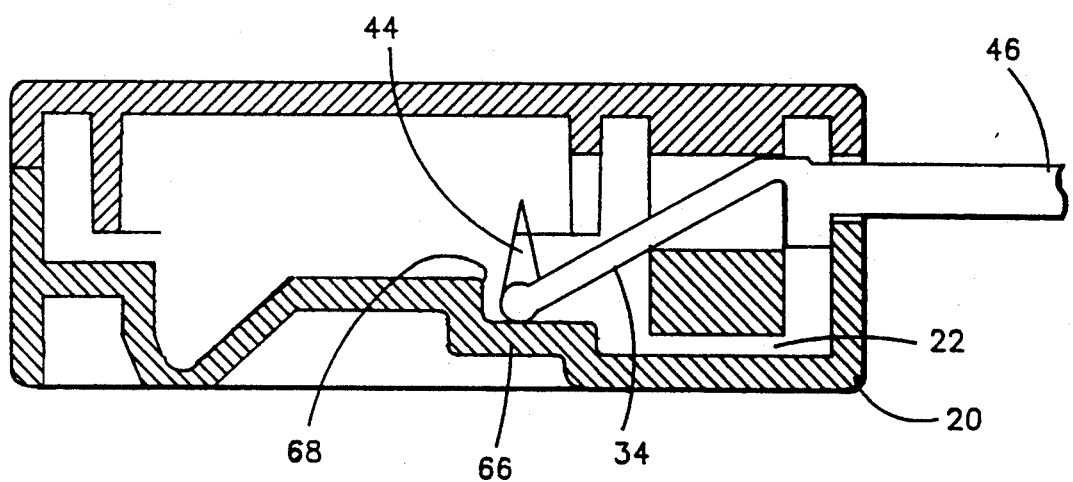
FIG.—6

ELUENT RELEASE SYSTEM AND AUTOMATED ASSAY DEVICE

TECHNICAL FIELD

The field of this invention is self-contained devices for quantitative measurements of analytes.

BACKGROUND

As more conditions have been capable of treatment, there has been an increasing interest in diagnosis. The diagnosis need not be related solely to a diseased condition, but also monitoring therapeutic dosages administered for such conditions. For the most part, this requires samples being transferred to a clinical laboratory, where skilled technical help is available, and the analyte could be measured accurately. However, in many instances it is desirable to have means for measuring a particular analyte at a doctor's office, a counseling service, or at home.

For determinations at home, it is necessary that the methodology be simple, free of sophisticated measurements, require a minimum of handling of reagents and mixing, as well as a minimum of accurate timing.

Toward this end a device has been recently described in U.S. Pat. No. 4,959,324. In this device, an eluent chamber is provided, where the eluent is maintained in a scorable container. Movement of a slide results in the puncture of the container, where the eluent is then released to be absorbed by a bibulous member. Despite the fact that the eluent container sits above a well into which the eluent is to flow, it is found that in many cases upon scoring or ripping of the container, the eluent is not released into the well. This results in a failure of the device, which is unacceptable for commercial application. It is therefore desirable to find means which allows for the assured transfer of the eluent from the container to the well to allow for the assay to be carried out.

Relevant Literature

U S. Pat. No. 4,959,324 describes the subject device prior to modification. See also references cited therein.

SUMMARY OF THE INVENTION

A device is provided, where the device employs a continuous flow path having at least three regions, a fluid transport region, a sample region, a measuring region and optionally a mixing region. The device comprises an elevated eluent-containing scorable container and a slide, which serves to score and rip open the container and release the eluent into a well in which said fluid transport region member extends. Means are provided for overcoming resistance to flow ensuring that the eluent is released from the container into the well.

BRIEF DESCRIPTION OF THE DRAWINGS

FIG. 1 comprises FIGS. A, B and C, where

FIG. 1A is a perspective view of a cover plate according to the subject invention;

FIG. 1B is an exploded view of the base plate and slide of a device according to the subject invention in the initial position prior to moving the slide; and FIG. 1C is an exploded view of the base plate and slide in the final position subsequent to the movement of the slide;

FIGS. 4, 5 and 6 are end cross-sectional views of an alternative embodiment for eluent release in the initial position, intermediate position and final position.

DESCRIPTION OF THE SPECIFIC EMBODIMENTS

Figure 2:
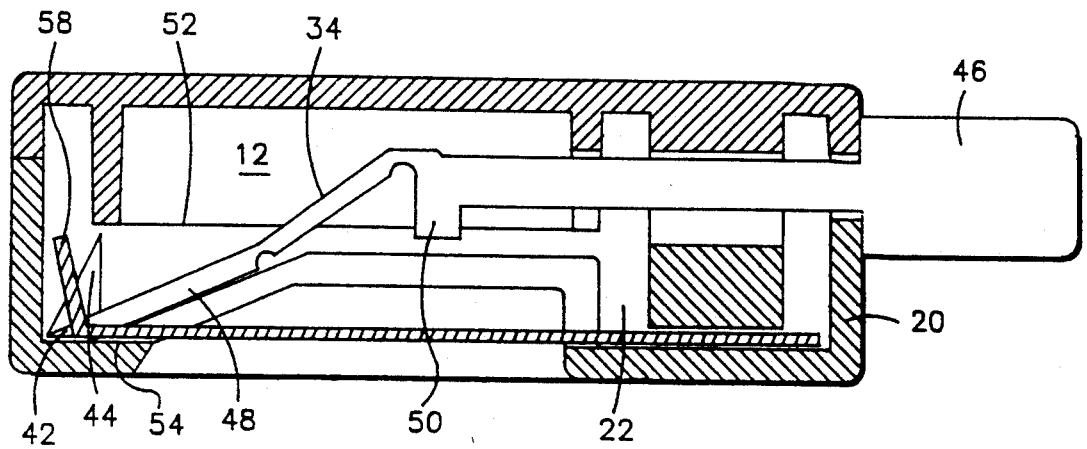
FIG. 2 is an end cross-sectional view of the scorable container penetration device in its initial position.

Apparatus are provided for the measurement of an analyte employing a continuous flow path, which has a sample receiving region as an internal region, which is brought into contact with the adjacent two regions to serve as a bridge. The device is substantially self-contained in including most or all reagents necessary for determination of an analyte and includes as part of the device a scorable container, which provides the eluent for transport of reagent components and products involved in the assay. Ripping or scoring means are provided for releasing the eluent from the container into a well. A fluid transport bibulous member extends into the well t serve as an absorbent conduit for transport of the eluent through the other bibulous members of the assay flow-path.

The apparatus comprises a flow-path which is primarily divided into three parts, a bibulous short element which serves by capillary action to wick or transport reagent solution to the sample receiving element; the sample receiving element, which is ordinarily a pad, which may be of any shape, but serves to act as a bridge between the transport element and the third bibulous element, the measuring element. The first and third elements are conveniently bibulous strips of any convenient material, which may or may not comprise reagents non-covalently or covalently bound.

A slide is employed to move the sample receiving element from a first position where the sample receiving element receives the sample, to a second position where the sample receiving element serves as a bridge between the two other elements of the flow-path. Means may be provided for removing excess fluid from the sample receiving element as it moves from the first to the second position. For example, by having a region in the path of a slide which is narrowed, so as to remove unabsorbed sample medium, without significantly squeezing the sample receiving element, the amount of sample absorbed by the sample receiving element can be relatively accurately reproduced. The narrowing may be as a result of a convexity, such as a rod in relief, roller, or other convenient scraping means. The narrowing of the path should provide a space about equal to or slightly less than the wet thickness of the sample receiving element. The slide may serve to move the sample receiving element as well as metering the amount of fluid absorbed by the sample receiving element.

In addition, the slide serves to release the eluent solution from a sealed pouch situated in a chamber above a well. The slide is provided with means to score the pouch and release the fluid into the underlying well. The scoring means may be sharp teeth, abrasive material, knife like edge(s), pins, etc. The teeth protrude upward from a support. Means are provided associated with the slide to ensure that the eluent solution is released from the pouch into the underlying well to make contact with the transport element which extends into the well.

A first means for ensuring eluent release is a wicking means, where a bibulous absorbent strip extends up through a groove in the support member of the scoring means at one end of the strip and extends into the buffer well proximal to the transport element at the other end of the strip. The scoring element moves from a first position out of contact with the container, where it brings with it the first end of the eluent release absorbent strip. The scoring means as it is pulled from its initial to its final position moves along a path involving an initial upward incline in scoring contac with the container followed by a substantially horizontal path while scoring the container. As the scoring means scores the container and opens the container, the eluent release absorbent strip extends into the container, so as to initiate flow of the eluent into the well.

Alternatively, one may provide a different path for the scoring means, where the scoring means of the slide moves up an incline to come into scoring contact with the container, continues to move horizontally and score the container and then snaps down below the intermediate position drawing the fluid down and initiating flow. The sudden drop of the arm results in a shock to the fluid overcoming the resistance to flow.

Where blood is the sample, means may be provided for removing red blood cells or other cells from the blood to provide plasma to the sample receiving means. For this purpose, filters may be provided in an orifice in a plate above the sample receiving member. The sample is added to the orifice where it flows through the filters, where the cells are removed, and then the plasma is absorbed by the sample receiving element. Various packings or sieving depth filters may be employed, which include glass fibers, cellulose filters treated with red blood cell capturing agents, glass fiber filters or synthetic fiber filters. Combinations of coarse and fine filters may be employed or asymmetric membranes may be employed.

The entire flow-path may have a length of about 25 to 200 mm, more usually from about 50 to 150 mm, preferably about 100 mm. About 25% to 90% of the length of the flow-path will be the measurement region comprising the quantitation zone, optionally a mixing zone and/or a threshold value zone. The mixing and/or threshold value zone would generally be from about 5% to 35% of the flow-path. The strips which provide for a flow of fluid to and from the sample receiving element may be the same or different length and will generally be from about 5 to 25 mm, more usually about 10% to 20% each of the length of the flow-path. The upstream strips may be part of the measurement region strip or may include an independent entity other than the measurement region. Alternatively, the upstream strip may be used to control the threshold value by removing a predetermined amount of a reagent related to the amount of analyte, which reagent is part of a signal producing system. The sample receiving element will generally be from about 1% to 10%, more usually from about 2% to 8% of the length of the flow-path; the longer the flow-path, the larger the sample receiving element will usually be.

The width of the strips may be varied widely, usually being at least about 2 mm and not more than about 10 mm, preferably from about 3 to 7 mm. The two strips adjacent the sample receiving element will usually each overlap the sample receiving element by at least about 0.2 mm and not more than about 2 mm, usually about 1 mm, being primarily a matter of convenience, so long as the two strips are not in direct fluid communication.

The measuring element will be an extended member, which allows for flow of the reagent solution through the measuring element, by means of capillary action. The measuring element may include an intermediate strip proximal to the sample receiving element which allows for flow from the sample receiving element to a region to which reagent is bound and serves as the region where signal is produced. This intermediate region may serve a plurality of purposes, providing mixing, a threshold value by reacting with a predetermined amount of reagent, providing for reactions associated with signal production, and the like.

Analyte is determined by the distance color is formed in the measurement region. Depending upon the nature of the assay, various signal producing systems and protocols may be employed. Where the analyte serves as an enzyme substrate, such as cholesterol and glucose, to produce hydrogen peroxide, one may use to produce the signal a dye produced from two components where reaction is initiated by peroxidase and hydrogen peroxide. By having the hydrogen peroxide generated upstream from the measurement region and having one of the dye components bound to the strip and peroxidase and the other component in the eluent, the distance to which color is produced will be related to the amount of analyte in the sample.

Alternatively, one may have a competitive protocol, where the complementary member of a specific binding pair is bound in the measurement region, the other member of the pair being the analyte. By having a conjugate of analyte and enzyme compete with analyte for the complementary binding member, the distance the conjugate migrates will be related to the amount of analyte in the sample. By flooding the measurement region with an enzyme substrate which produces an insoluble dye, one can relate the distance of the colored border to the amount of analyte in the sample.

For further understanding of the invention, the drawings will now be considered.

FIG. 1 is an exploded view of the device in two positions, where FIG. 1A is a cover plate and FIG. 1B and 1C are the slide and base plate, with the slide in the initial position and final position. The cover plate 10 comprises a chamber 12 in which the eluent is contained by sealing the lower surface of the chamber with a polyfoil seal or the like. An orifice 14 extending through the cover plate 10 is bevelled for receiving sample. A viewing slot 16 extends parallel to the side of the cover plate and permits observation of the measurement region. At the top of the viewing slot 16 is an indicator hole 18, which changes color when the test is complete to inform the user that a reading may be taken.

The base plate 20 comprises well 22 and channel 24 for receiving the measurement region strip 26. Transport region strip 28 extends into the well and over slide 30. Sample pad 32 is supported on the slide 30 and is positioned underneath orifice 14 in the initial position. Orifice 14 may include blood separation means, (not shown), for removing red blood cells from the sample.

The slide 30 has two arms: a first arm 34 serving as the scoring arm and a second arm 36 serving as a sample receiving element supporting arm. The scoring arm 34 comprises first and second separated beams 38 and 40 joined at one end by rod 42 normal to said beams, which supports scoring teeth 44. The other ends of beams 38 and 40 are joined to handle 46, which serves to move the slide. The beams 38 and 40 are shaped so as to have an inclined section 48 and a small leg 50, so that the scoring elements (teeth) are initially below the eluent containing pouch. The slide is a flexible material, e.g., elastomeric plastic, so as to be able to move under pressure and return to is original position when the pressure is released. Useful materials include any of the thermoplastics, including polyethylene, polypropylene, ABS and polystrene. By moving handle 46 from its initial position with the sample receiving element 32 under orifice 14 to its final position as shown in FIG. 1C, the sample receiving element 32 now serve to bridge measurement region strip 26 and transport region strip 28, while the scoring teeth 44 open the eluent pouch to allow for the release of the eluent.

Figure 3:
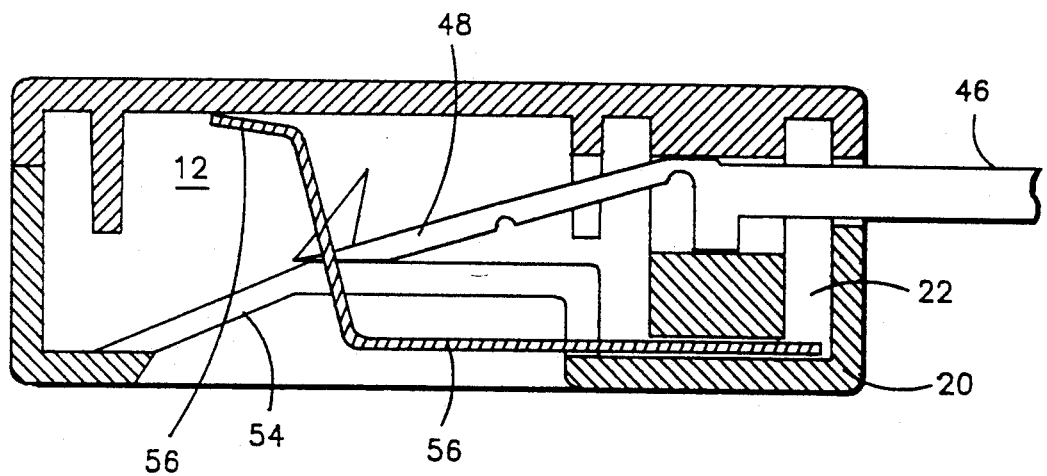
FIG. 3 is an end cross-sectional view of the device according to FIG. 2 in its penetration position.

FIGS. 2-6 will now be considered, where the modifications for ensuring substantially complete success for eluent release is provided. The scoring arm 34 has inclined section 48 terminating in scoring teeth 44. The base plate 20 is shaped so as to provide an inclined support 54 for raising the scoring arm 34 into scoring contact with foil seal 52.

A bibulous strip 56 serves for buffer release. The bibulous strip will be of a convenient size in accordance with the size and shape of the device. For devices described previously, the bibulous strip is about 4 mm wide and about 3 cm long. The bibulous strip terminates at one end in a tongue 58, which extends through a groove in the rod 42. Thus, the tongue slidably extends through the rod 42, so that rod 42 may move along bibulous strip 56 pushing bibulous strip 56 up into chamber 12. The bibulous strip 56 extends from the tongue in a line parallel to the end of the subject device into the portion of the well 22 in which transport region strip 28 extends. The handle 46 is pulled away from the base plate 20 causing the scoring arm 48 to move along the incline section 54 and to score the foil seal 52. At the same time, bibulous strip 56 will be forced upwards into the chamber 12, where it may serve to initiate eluent solution flow to well 22.

In FIGS. 4-6, an alternative embodiment is provided, where the track for the rod 42 with the scoring teeth 44 has been modified. The base plate is shaped so as to provide a pocket 60 for rod 42 to reside in the initial position. The pocket has an incline region 62, a relatively flat region 64 which terminates to allow for the rod 42 to rapidly drop to a second flat region 66 whose surface is below the level of flat region 64. In operation, the scoring arm 34 is made of a resilient flexible material which allows for movement of the arm under pressure and restoration of the original shape upon release of pressure. As before, various elastomeric plastics may be used for providing such an arm.

In operation, as shown in FIG. 5, the handle 46 is moved away from the base plate 20 moving the scoring arm 34, as well as rod 42 upwards, so as to be on the surface of the flat region 64. This brings the scoring teeth 44 in contact with the foil seal 52, opening the seal to permit the release of the eluent solution. Movement along the surface of the flat region 64 continues to score the foil seal further opening the pouch. When the pouch has been scored substantially its entire length, rod 42 will be at the end of the surface of flat region 64 where it ends 68, the region drops off to a second flat region 66. As shown in FIG. 6, the handle 46 is now extended at its final distance from the base plate 20 and scoring arm 34 is now in its lower position along the surface of flat region 66, where the sudden drop of the scoring arm 34 and scoring teeth 44 at point 68 results in the flow of the eluent solution into well 22.

By employing the subject devices, incidence of failure of up to 25% because of lack of eluent flow have been substantially reduced to 2% or fewer. Thus, the subject devices allow for substantially enhanced reliability when used for the detection of analytes. Since the subject devices are intended for use by non-technical people, particularly in the home, it is very important that where blood or other sample is to be taken, it not have to be repetitively taken because the device fails. Thus, by preventing failures due to the failure of the eluent solution to flow into the well, users can have greater assurance of reliability in obtaining an accurate result and without having to throw away the device. In addition, the supplier will not have to deal with significant numbers of returns of devices, which can greatly enhance the cost of the device.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. In a self-contained analyte measuring device, comprising:
    a housing comprising a well, a flow path, two bibulous spaced apart strips wherein said path holds said strips in position and defines a space between said strips, the end of one of said strips extending into said well, and a structure for receiving a slide proximal to one end of said housing;
    an orifice for receiving a sample displaced from and substantially aligned with the space between said two bibulous strips;
    a slide element in said structure comprising: a sample receiving element positioned under said orifice when said slide element is in an initial position, and positioned in said space when said slide is in a final position; and scoring means for releasing a liquid into said well when said slide is moved from its initial position to its final position; and,
    a scorable container enclosing said liquid in a compartment located above said wall, where upon scoring of said container, said liquid can be released into said well;
    the improvement which comprises:
    means for overcoming resistance of said liquid from flowing into said well by initiating flow of said liquid resulting from movement of said slide, said overcoming resistance means operating in connection with said scoring means, said means for overcoming resistance including at least one of shocking means and wicking means.

2. A device according to claim 1, wherein said scoring means comprises sharp scoring elements supported by a support member at one end of said slide, said support member having a slot; and
    said overcoming resistance means comprises a bibulous strip extending through said slot at one end of said slide and extending into said well proximal to said bibulous strip extending into said well.

3. A device according to claim 1, wherein said housing defines a path for said scoring means of said slide when said slide moves from said initial position to said final position, wherein said path defines an inclined upward path to move said scoring means into scoring position for said scorable container and an horizontal path for maintaining said scoring means in said scoring position.

4. A device according to claim 1, wherein said housing defines said overcoming resistance means and includes a path for said scoring means of said slide when said slide moves from said initial position to said final position, wherein said path defines an inclined upward path to move said scoring means into scoring position for said scorable container, an horizontal path for maintaining said scoring means in said scoring position, and a drop to a lower level at a time prior to said final position.

5. A device according to claim 1, wherein said slide is composed of a flexible plastic.

6. A device according to claim 1, wherein said slide comprises two arms: (1) a sample receiving element arm; and (2) a scoring member supporting arm.

7. A device according to claim 6, wherein said scoring member supporting arm comprises two spaced apart beams terminating in a rod normal to said beams, and sharp scoring elements protruding upwards from said rod.

* * * * *